United States Patent [19]
Diamandis et al.

[11] Patent Number: 6,071,726
[45] Date of Patent: *Jun. 6, 2000

[54] METHOD, REAGENTS AND KIT FOR DIAGNOSIS AND TARGETED SCREENING FOR P53 MUTATIONS

[75] Inventors: Eleftherios Diamandis, Toronto; James M. Dunn, Scarborough; John K. Stevens, Toronto, all of Canada

[73] Assignee: Visible Genetics Inc., Toronto, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/765,626

[22] PCT Filed: Jul. 7, 1995

[86] PCT No.: PCT/US95/08605

§ 371 Date: Dec. 27, 1996

§ 102(e) Date: Dec. 27, 1996

[87] PCT Pub. No.: WO96/01909

PCT Pub. Date: Jan. 25, 1996

Related U.S. Application Data

[63] Continuation-in-part of application No. 08/271,946, Jul. 8, 1994, Pat. No. 5,545,527, and a continuation-in-part of application No. 08/388,381, Feb. 14, 1995, Pat. No. 5,552,283.

[51] Int. Cl.[7] .............................. C12P 19/34; C12Q 1/68; G01N 33/53; C07H 21/04
[52] U.S. Cl. .............................. 435/91.2; 435/6; 435/7.1; 536/24.3; 536/23.1; 536/24.33
[58] Field of Search ..................... 435/6, 91.2; 536/24.3, 536/24.33, 23.1

[56] References Cited

U.S. PATENT DOCUMENTS 5,403,707 4/1995 Atwood et al. .
5,545,527 8/1996 Stevens et al. ........................ 435/6
5,552,283 9/1996 Diamandis et al. .................... 435/6

OTHER PUBLICATIONS

Toguchida et al. new England Journal of Medicine 326: 1301–1308, 1992.
Kohler et al. Society for Gynecologic Oncologists 23rd Annual Meeting Mar. 15–18, p. 40, 1992.
Runnenbaum et al. PNAS 88: 10657–61, 1991.

*Primary Examiner*—Kenneth R. Horlick
*Assistant Examiner*—Jeffrey Siew
*Attorney, Agent, or Firm*—Oppedahl & Larson LLP

[57] ABSTRACT

Rapid and cost effective diagnosis of p53 mutations of a sample of patients is achieved by employing a selected plurality of diagnostic tools, in a hierarchy of increasing accuracy and cost per tool, in which each tool detects essentially no false positives. Diagnostic tests that may be included among the plurality of tests selected include, in order of increasing accuracy and cost:

(a) immunoassays,
(b) analysis of DNA from a patient sample by quantitative amplification of p53 exons using amplification primers complementary to intron regions flanking each exon and examination of the length or quantity of each amplified fragment for nucleotide insertions or deletions relative to the normal p53 gene. Preferably, the amplification primers are multiplexed so that more than one DNA fragment is amplified in a single vessel, using sets of primers which provide gene fragments of distinctive lengths when used to amplify a normal p53 gene; and
(c) analysis of DNA from a patient sample by DNA sequencing of the p53 gene beginning with the sequencing of those regions most likely to harbor point mutations, and proceeding to sequence regions less likely to harbor point mutations.

21 Claims, 2 Drawing Sheets

```
HIERARCHY OF P53 DIAGNOSIS

LEVEL 1: IMMUNOASSAY

PATIENTS ANALYZED:     100
    PATIENTS DIAGNOSED:     15

ACCURACY:      LOW
    COST:          LOW
    SPECIFICITY:   HIGH

LEVEL 2: DNA FRAGMENT LENGTH/QUANTITY ANALYSIS

PATIENTS ANALYZED:     85
    PATIENTS DIAGNOSED:    26

ACCURACY:      MEDIUM
    COST:          MEDIUM
    SPECIFICITY:   HIGH

LEVEL 3: DNA SEQUENCING

PATIENTS ANALYZED:     59
    PATIENTS DIAGNOSED:    59

ACCURACY:      HIGH
    COST:          HIGH
    SPECIFICITY:   HIGH
```

HIERARCHY OF P53 DIAGNOSIS

LEVEL 1: IMMUNOASSAY

| | |
|---|---|
| PATIENTS ANALYZED: | 100 |
| PATIENTS DIAGNOSED: | 15 |
| ACCURACY: | LOW |
| COST: | LOW |
| SPECIFICITY: | HIGH |

LEVEL 2: DNA FRAGMENT LENGTH/QUANTITY ANALYSIS

| | |
|---|---|
| PATIENTS ANALYZED: | 85 |
| PATIENTS DIAGNOSED: | 26 |
| ACCURACY: | MEDIUM |
| COST: | MEDIUM |
| SPECIFICITY: | HIGH |

LEVEL 3: DNA SEQUENCING

| | |
|---|---|
| PATIENTS ANALYZED: | 59 |
| PATIENTS DIAGNOSED: | 59 |
| ACCURACY: | HIGH |
| COST: | HIGH |
| SPECIFICITY: | HIGH |

FIG. 1

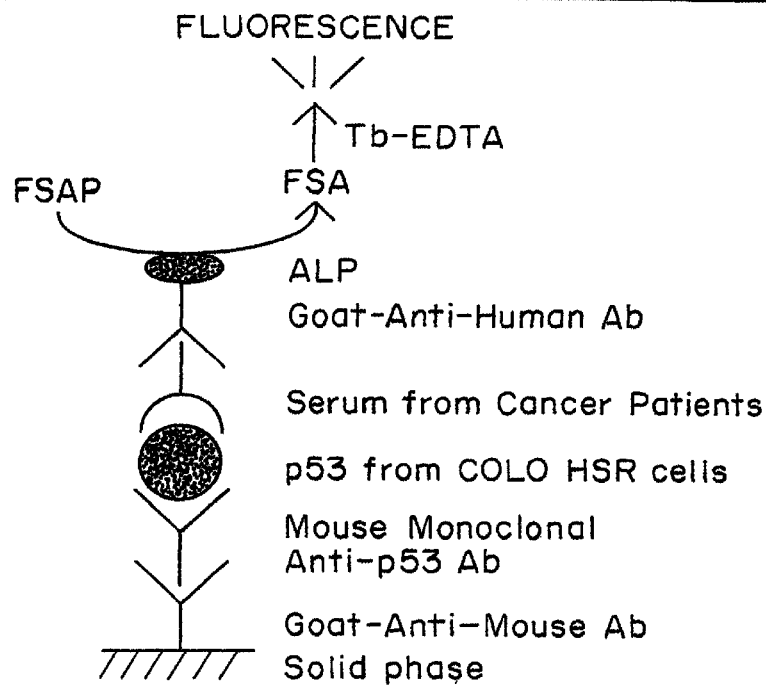
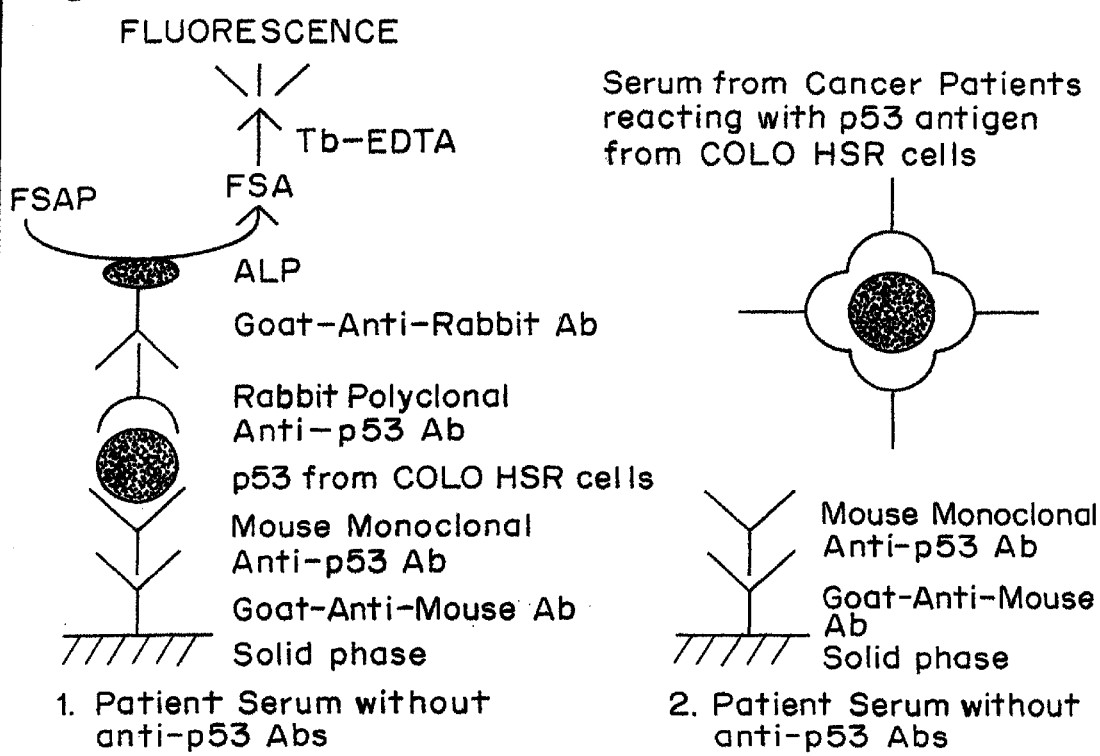

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: genomic DNA (iii) HYPOTHETICAL: no -continued (iv) ANTI-SENSE: yes (v) FRAGMENT TYPE: internal (vi) ORIGINAL SOURCE:
             (A) ORGANISM: human (ix) FEATURE:
             (A) NAME/KEY: primer for exon 1 of human p53 gene (xi) SEQUENCE DESCRIPTION: SEQ ID NO:1:

CGGATTACTT GCCCTTACTT GTCA                                                    24

(2) INFORMATION FOR SEQ ID NO:2:

(i) SEQUENCE CHARACTERISTICS:
             (A) LENGTH: 19
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 1 of human p53 gene (xi) SEQUENCE DESCRIPTION: SEQ ID NO:2:

CCCCAGCCCC AGCGATTTT                                                          19

(2) INFORMATION FOR SEQ ID NO:3:

(i) SEQUENCE CHARACTERISTICS:
             (A) LENGTH: 20
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
             (A) ORGANISM: human (ix) FEATURE:
             (A) NAME/KEY: primer for exon 3 of human p53 gene (xi) SEQUENCE DESCRIPTION: SEQ ID NO:3:

CATGGGACTG ACTTTCTGCT                                                         20

(2) INFORMATION FOR SEQ ID NO:4:

(i) SEQUENCE CHARACTERISTICS:
             (A) LENGTH: 19
             (B) TYPE: nucleic acid
             (C) STRANDEDNESS: single
             (D) TOPOLOGY: linear (ii) MOLECULE TYPE: genomic DNA -continued (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 3 of human p53 gene (xi) SEQUENCE DESCRIPTION: SEQ ID NO:4:

GGACGGCAAG GGGGACTGT                                                   19

(2) INFORMATION FOR SEQ ID NO:5:

(i) SEQUENCE CHARACTERISTICS:
            (A) LENGTH: 24
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
             (A) ORGANISM: human (ix) FEATURE:
             (A) NAME/KEY: primer for exon 4 of human p53 gene (xi) SEQUENCE DESCRIPTION: SEQ ID NO:5:

CTGGTCCTCT GACTGCTCTT TTCA                                             24

(2) INFORMATION FOR SEQ ID NO:6:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 4 of human p53 gene (xi) SEQUENCE DESCRIPTION: SEQ ID NO:6:

AAAGAAATGC AGGGGGATAC GG                                               22

(2) INFORMATION FOR SEQ ID NO:7:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
             (A) ORGANISM: human (ix) FEATURE:
             (A) NAME/KEY: primer for exon 5 of human p53 gene (xi) SEQUENCE DESCRIPTION: SEQ ID NO:7:

TGTTCACTTG TGCCCTGACT                                           20

(2) INFORMATION FOR SEQ ID NO:8:

(i) SEQUENCE CHARACTERISTICS:
             (A) LENGTH: 20
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 5 of human p53 gene (xi) SEQUENCE DESCRIPTION: SEQ ID NO:8:

CAGCCCTGTC GTCTCTCCAG                                           20

(2) INFORMATION FOR SEQ ID NO:9:

(i) SEQUENCE CHARACTERISTICS:
             (A) LENGTH: 20
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
             (A) ORGANISM: human (ix) FEATURE:
             (A) NAME/KEY: primer for exon 6 of human p53 gene (xi) SEQUENCE DESCRIPTION: SEQ ID NO:9:

CTGGGGCTGG AGAGACGACA                                           20

(2) INFORMATION FOR SEQ ID NO:10:

(i) SEQUENCE CHARACTERISTICS:
             (A) LENGTH: 19
             (B) TYPE: nucleic acid
             (C) STRANDEDNESS: single (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
              (A) ORGANISM: human (ix) FEATURE:
              (A) NAME/KEY: primer for exon 6 of human p53 gene (xi) SEQUENCE DESCRIPTION: SEQ ID NO:10:

GGAGGGCCAC TGACAACCA                                                    19

(2) INFORMATION FOR SEQ ID NO:11:

(i) SEQUENCE CHARACTERISTICS:
              (A) LENGTH: 19
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
              (A) ORGANISM: human (ix) FEATURE:
              (A) NAME/KEY: primer for exon 9 of human p53 gene (xi) SEQUENCE DESCRIPTION: SEQ ID NO:11:

GCGGTGGAGG AGACCAAGG                                                    19

(2) INFORMATION FOR SEQ ID NO:12:

(i) SEQUENCE CHARACTERISTICS:
              (A) LENGTH: 22
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
              (A) ORGANISM: human (ix) FEATURE:
              (A) NAME/KEY: primer for exon 9 of human p53 gene (xi) SEQUENCE DESCRIPTION: SEQ ID NO:12:

AACGGCATTT TGAGTGTTAG AC                                                22

(2) INFORMATION FOR SEQ ID NO:13:

(i) SEQUENCE CHARACTERISTICS:
              (A) LENGTH: 23

(B) TYPE: nucleic acid
       (C) STRANDEDNESS: single
       (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
       (A) ORGANISM: human (ix) FEATURE:
       (A) NAME/KEY: primer for exon 10 of human p53 gene (xi) SEQUENCE DESCRIPTION: SEQ ID NO:13:

TGATCCGTCA TAAAGTCAAA CAA                                           23

(2) INFORMATION FOR SEQ ID NO:14:

(i) SEQUENCE CHARACTERISTICS:
       (A) LENGTH: 21
       (B) TYPE: nucleic acid
       (C) STRANDEDNESS: single
       (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
       (A) ORGANISM: human (ix) FEATURE:
       (A) NAME/KEY: primer for exon 10 of human p53 gene (xi) SEQUENCE DESCRIPTION: SEQ ID NO:14:

GTGGAGGCAA GAATGTGGTT A                                             21

(2) INFORMATION FOR SEQ ID NO:15:

(i) SEQUENCE CHARACTERISTICS:
       (A) LENGTH: 21
       (B) TYPE: nucleic acid
       (C) STRANDEDNESS: single
       (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
       (A) ORGANISM: human (ix) FEATURE:
       (A) NAME/KEY: primer for exon 11 of human p53 gene (xi) SEQUENCE DESCRIPTION: SEQ ID NO:15:

GGCACAGACC CTCTCACTCA T                                             21

(2) INFORMATION FOR SEQ ID NO:16:

```
     (i) SEQUENCE CHARACTERISTICS:
         (A) LENGTH: 21
         (B) TYPE: nucleic acid
         (C) STRANDEDNESS: single
         (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (A) NAME/KEY: primer for exon 11 of human p53 gene (xi) SEQUENCE DESCRIPTION: SEQ ID NO:16:

TGCTTCTGAC GCACACCTAT T                                          21

(2) INFORMATION FOR SEQ ID NO:17:

(i) SEQUENCE CHARACTERISTICS:
         (A) LENGTH: 20
         (B) TYPE: nucleic acid
         (C) STRANDEDNESS: single
         (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
         (A) ORGANISM: human (ix) FEATURE:
         (A) NAME/KEY: primer for exon 2 of human p53 gene (xi) SEQUENCE DESCRIPTION: SEQ ID NO:17:

ACCCAGGGTT GGAAGCGTCT                                            20

(2) INFORMATION FOR SEQ ID NO:18:

(i) SEQUENCE CHARACTERISTICS:
         (A) LENGTH: 22
         (B) TYPE: nucleic acid
         (C) STRANDEDNESS: single
         (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (A) NAME/KEY: primer for exon 2 of human p53 gene (xi) SEQUENCE DESCRIPTION: SEQ ID NO:18:

GACAAGAGCA GAAAGTCAGT CC                                         22
```

```
(2) INFORMATION FOR SEQ ID NO:19:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (A) NAME/KEY: primer for exon 8 of human p53 gene (xi) SEQUENCE DESCRIPTION: SEQ ID NO:19:

GACAAGGGTG GTTGGGAGTA GATG                                              24

(2) INFORMATION FOR SEQ ID NO:20:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 8 of human p53 gene (xi) SEQUENCE DESCRIPTION: SEQ ID NO:20:

GCAAGGAAAG GTGATAAAAG TGAA                                              24

(2) INFORMATION FOR SEQ ID NO:21:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (A) NAME/KEY: primer for exon 7 of human p53 gene (xi) SEQUENCE DESCRIPTION: SEQ ID NO:21:

GGCGACAGAG CGAGATTCCA                                                   20
```

(2) INFORMATION FOR SEQ ID NO:22:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 7 of human p53 gene (xi) SEQUENCE DESCRIPTION: SEQ ID NO:22:

GGGTCAGCGG CAAGCAGAGG                                            20

(2) INFORMATION FOR SEQ ID NO:23:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (A) NAME/KEY: sequencing primer for exon 2 of human p53 gene (xi) SEQUENCE DESCRIPTION: SEQ ID NO:23:

CCAGGGTTGG AAGCGTCTC                                             19

(2) INFORMATION FOR SEQ ID NO:24:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: sequencing primer for exon 2 of human p53 gene (xi) SEQUENCE DESCRIPTION: SEQ ID NO:24:

```
GCTAGGGGGC TGGGGTTGG                                                    19

(2) INFORMATION FOR SEQ ID NO:25:

(i) SEQUENCE CHARACTERISTICS:
         (A) LENGTH: 18
         (B) TYPE: nucleic acid
         (C) STRANDEDNESS: single
         (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (A) NAME/KEY: sequencing primer for exon 3 of human p53 gene (xi) SEQUENCE DESCRIPTION: SEQ ID NO:25:

ATGGGTGAAA AGAGCAGT                                                     18

(2) INFORMATION FOR SEQ ID NO:26:

(i) SEQUENCE CHARACTERISTICS:
         (A) LENGTH: 18
         (B) TYPE: nucleic acid
         (C) STRANDEDNESS: single
         (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
         (A) ORGANISM: human (ix) FEATURE:
         (A) NAME/KEY: sequencing primer for exon 4 of human p53 gene (xi) SEQUENCE DESCRIPTION: SEQ ID NO:26:

GGGGCTGAGG ACCTGGTC                                                     18

(2) INFORMATION FOR SEQ ID NO:27:

(i) SEQUENCE CHARACTERISTICS:
         (A) LENGTH: 18
         (B) TYPE: nucleic acid
         (C) STRANDEDNESS: single
         (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (A) NAME/KEY: sequencing primer for exon 4 of human p53 gene
```

(xi) SEQUENCE DESCRIPTION: SEQ ID NO:27:

ATACGGCCAG GCATTGAA                                              18

(2) INFORMATION FOR SEQ ID NO:28:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
            (A) ORGANISM: human (ix) FEATURE:
            (A) NAME/KEY: sequencing primer for exon 5 of human p53 gene (xi) SEQUENCE DESCRIPTION: SEQ ID NO:28:

CACTTGTGCC CTGACTTT                                              18

(2) INFORMATION FOR SEQ ID NO:29:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: sequencing primer for exon 5 of human p53 gene (xi) SEQUENCE DESCRIPTION: SEQ ID NO:29:

CCTGGGGACC CTGGGCAA                                              18

(2) INFORMATION FOR SEQ ID NO:30:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
            (A) ORGANISM: human (ix) FEATURE:
                (A) NAME/KEY: sequencing primer for exon 6 of human p53 gene (xi) SEQUENCE DESCRIPTION: SEQ ID NO:30:

TGGTTGCCCA GGGTCCCC                                                           18

(2) INFORMATION FOR SEQ ID NO:31:

(i) SEQUENCE CHARACTERISTICS:
                (A) LENGTH: 16
                (B) TYPE: nucleic acid
                (C) STRANDEDNESS: single
                (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
                (A) ORGANISM: human (ix) FEATURE:
                (A) NAME/KEY: sequencing primer for exon 6 of human p53 gene (xi) SEQUENCE DESCRIPTION: SEQ ID NO:31:

CCACTGACAA CCACCC                                                             16

(2) INFORMATION FOR SEQ ID NO:32:

(i) SEQUENCE CHARACTERISTICS:
                (A) LENGTH: 17
                (B) TYPE: nucleic acid
                (C) STRANDEDNESS: single
                (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
                (A) ORGANISM: human (ix) FEATURE:
                (A) NAME/KEY: sequencing primer for exon 7 of human p53 gene (xi) SEQUENCE DESCRIPTION: SEQ ID NO:32:

CTCCCCTGCT TGCCACA                                                            17

(2) INFORMATION FOR SEQ ID NO:33:

(i) SEQUENCE CHARACTERISTICS:
                (A) LENGTH: 17
                (B) TYPE: nucleic acid
                (C) STRANDEDNESS: single
                (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:

(A) ORGANISM: human (ix) FEATURE:
        (A) NAME/KEY: sequencing primer for exon 7 of human p53 gene (xi) SEQUENCE DESCRIPTION: SEQ ID NO:33:

TCAGCGGCAA GCAGAGG                                                      17

(2) INFORMATION FOR SEQ ID NO:34:

(i) SEQUENCE CHARACTERISTICS:
        (A) LENGTH: 17
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (A) NAME/KEY: sequencing primer for exon 8 of human p53 gene (xi) SEQUENCE DESCRIPTION: SEQ ID NO:34:

ATGGGACAGG TAGGACC                                                      17

(2) INFORMATION FOR SEQ ID NO:35:

(i) SEQUENCE CHARACTERISTICS:
        (A) LENGTH: 17
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: sequencing primer for exon 8 of human p53 gene (xi) SEQUENCE DESCRIPTION: SEQ ID NO:35:

CATAACTGCA CCCTTGG                                                      17

(2) INFORMATION FOR SEQ ID NO:36:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
            (A) ORGANISM: human (ix) FEATURE:
            (A) NAME/KEY: sequencing primer for exon 9 of human p53 gene (xi) SEQUENCE DESCRIPTION: SEQ ID NO:36:

GGA GGA GAC CAA GGG TGC                                                18

(2) INFORMATION FOR SEQ ID NO:37:

(i) SEQUENCE CHARACTERISTICS:
            (A) LENGTH: 17
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: sequencing primer for exon 9 of human p53 gene (xi) SEQUENCE DESCRIPTION: SEQ ID NO:37:

GGAAACTTTC CACTTGA                                                     17

(2) INFORMATION FOR SEQ ID NO:38:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
            (A) ORGANISM: human (ix) FEATURE:
            (A) NAME/KEY: sequencing primer for exon 10 of human p53 gene (xi) SEQUENCE DESCRIPTION: SEQ ID NO:38:

CCATCTTTTA ACTCAGGT                                                    18

(2) INFORMATION FOR SEQ ID NO:39:

(i) SEQUENCE CHARACTERISTICS:
            (A) LENGTH: 17
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: sequencing primer for exon 10 of human p53 gene (xi) SEQUENCE DESCRIPTION: SEQ ID NO:39:

CATGAAGGCA GGATGAG                                                      17

(2) INFORMATION FOR SEQ ID NO:40:

(i) SEQUENCE CHARACTERISTICS:
            (A) LENGTH: 17
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: yes (v) FRAGMENT TYPE: internal (vi) ORIGINAL SOURCE:
            (A) ORGANISM: human (ix) FEATURE:
            (A) NAME/KEY: sequencing primer for exon 11 of human p53 gene (xi) SEQUENCE DESCRIPTION: SEQ ID NO:40:

AGACCCTCTC ACTCATG                                                      17

(2) INFORMATION FOR SEQ ID NO:41:

(i) SEQUENCE CHARACTERISTICS:
            (A) LENGTH: 17
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: sequencing primer for exon 11 of human p53 gene (xi) SEQUENCE DESCRIPTION: SEQ ID NO:41:

CAAGCAAGGG TTCAAAG                                                      17

METHOD, REAGENTS AND KIT FOR DIAGNOSIS AND TARGETED SCREENING FOR P53 MUTATIONS

This application is a continuation-in-part of U.S. patent application Ser. No. 08/271,946 filed Jul. 8, 1994, now U.S. Pat. No. 5,545,527 and a continuation-in-part of U.S. patent application Ser. No. 08/388,381 filed Feb. 14, 1995, now U.S. Pat. No. 5,552,283.

BACKGROUND OF THE INVENTION

This application relates to a method, reagents and kit for diagnosis and targeted screening of mutation in p53 protein and mutation in the gene coding for the p53 protein (herein the "p53 gene") Such mutations are collectively referred to herein as "p53 mutations".

The evidence for the tumor suppressor activity of wild-type p53 is now extensive. Since its discovery in 1979 when it was found to be complexed with the SV40 large T antigen in SV40-transformed rodent cells the significance of p53 has slowly come to light. The protein appears to act as a transcription factor, and may be responsible for apoptosis of pre-cancerous cells. (Ziegler et al., "Sunburn and p53 in the onset of skin cancer", *Nature* 372: 773–776 (1994)) The DNA sequence of the 11 exons of the p53 gene is now known and close to 1000 papers were published on p53 in 1993.

P53 mutations are significant because they are found in an enormous variety of tumors. Among common tumors, about 70% of colorectal cancers, 50% of lung cancers, and up to 40% of breast cancers carry p53 gene mutations. p53 is also linked to cancers of the blood and lymph nodes, including Hodgkin's disease, T cell lymphoma and certain kinds of leukemia. Moreover, aberrant forms of the p53 gene are correlated with more aggressive tumors, metastasis and lower 5-year survival rates. Such reports have emerged for cancers of the colon, lung, cervix, bladder, prostate, breast and skin.

The serious consequences of p53 mutations mandates a method for detection and diagnosis of such mutations which is rapid and accurate and that can be performed at the earliest stage of tumor development. Toward this end, immunoassays and DNA assays for p53 mutations are known in the art. To date, however, neither method has been able to identify p53 mutations with a high degree of specificity and accuracy in a cost effective fashion. Those immunoassays that have been published identify only a small portion of those patients actually thought to be carrying the mutation.

Two general techniques of immunoassay have been employed. The first technique is an indirect method which detects anti-p53 antibodies that arise in some patients who have p53 mutations. Immunoassay tests for detecting anti-p53 antibodies in patient sera are currently based on radioactive labeling, immunoprecipitation and immunoblotting. All these methods are qualitative and time consuming and thus not suitable for screening large number of samples. (Angelopoulou et al., "Autoantibodies against the p53 tumor suppressor gene product quantified in cancer patient serum with time-resolved immunofluorometry", *Cancer J* 6(6): 315–321 (1993)).

The second technique of immunoassay directly detects mutant p53 protein. Such methods have been disclosed in at least two publications. Bartek et al. disclosed an enzyme-linked immunosorbent assay for p53 which was applied for the measurement of p53 in tumor tissue extracts (*Oncogene,* 6: 1699–1703 (1991)). Hassapoglidou et al. developed a monoclonal antibody useful for direct detection of mutant p53. (*Oncogene* 8: 1501–1509 (1993).)

DNA analysis of p53 mutations has been reported using at least two techniques. First, single stranded conformational polymorphism was used to detect mutant p53 by Kuypers et al. ("Detection of point mutations in DNA using capillary electrophoresis in a polymer network", *J. Chromatography* 621: 149–56 (1993)) and by Felix et al ("Absence of hereditary p53 mutations in 10 familial leukemia pedigrees", *J Clin Invest* 90: 653–8 (1992)). Second, actual genomic DNA sequencing diagnosis was performed on relatively small groups of patients by Toguchida et al. ("Prevalence and spectrum of germline mutations of the p53 gene among patients with sarcoma", *N Engl J Med* 326: 1301–8 (1992)) and by Malkin et al. ("Germline mutations of the p53 tumor-suppressor gene in children and young adults with second malignant neoplasms", *N Engl J Med* 326: 1309–15 (1992)). The cDNA sequence of a larger group of patients (over 400) was reported in a Pharmacia LKB meeting publication (Andell et al. "A new approach in automated DNA sequencing to analyse the p53 gene in a large number of breast cancer patients", Pharmacia LKB meeting literature, 1994) These rapid DNA-based techniques have been used to detect mutations, but because they are so labor intensive, that large-scale screening tests are impractical (Harris et al., "Clinical implications of the p53 tumor-suppressor gene", *N Engl J Med* 329:1318–1327 (1993)).

Thus, the existing methods of diagnosis have been frustratingly unsatisfactory. Researchers have used either immunoassay or DNA analytical methods to diagnose p53 mutation, even though such tests result in numerous false negatives. A method is required for rapid and cost effective diagnosis of p53 mutation in the millions of individuals who develop potentially life threatening malignancies each year.

It is an object of this invention to provide a method for rapid and cost effective diagnosis of p53 mutations in a sample of patients.

It is a further object of this invention to provide DNA sequencing and amplification primers specific for analysis of the p53 gene from a patient sample.

It is a further object of this invention to provide kits of DNA oligonucleotides for amplification and sequencing of the p53 gene of a patient.

It is a further object of this invention to provide a method of generating a p53 mutation report which is used to provide appropriate genetic counseling to the patient and family upon whom the test is performed.

SUMMARY OF THE INVENTION

In accordance with the present invention, rapid and cost effective diagnosis of p53 mutations of a sample of patients is achieved by employing a selected plurality of diagnostic tools, in a hierarchy of increasing accuracy and cost per tool, in which each tool detects essentially no false positives. Diagnostic tests that may be included among the plurality of tests selected include, in order of increasing accuracy and cost:

(a) immunoassays, particularly immunoassays for anti-p53 antibodies present in a patient sample;

(b) analysis of DNA from a patient sample by quantitative amplification of p53 exons using amplification primers complementary to intron regions flanking each exon and examination of the length or quantity of each amplified fragment for nucleotide insertions or deletions relative to the normal p53 gene. Preferably, the amplification primers are multiplexed so that more than one DNA fragment is amplified in a single vessel, using sets of primers which provide gene fragments of distinctive lengths when used to amplify a normal p53 gene; and (c) analysis of DNA from a patient sample by DNA sequencing of the p53 gene beginning with the sequencing of those regions most likely to harbor point mutations, and proceeding to sequence regions less likely to harbor point mutations.

The present invention includes a multitude of amplification and sequencing primers. These primers, taken individually or as part of kits for the detection of p53 mutations represent a further aspect of the present invention. Particularly preferred primers constitute sets that are compatible for coamplification and that produce amplified DNA fragments of distinctive lengths from other fragments amplified in the same set.

The information obtained in the test is used to generate a report which is used to provide appropriate genetic counseling to the patient and family upon whom the test is performed. The generation of such reports, which may be in the form of a printed report, an electronic communication, such as a facsimile or electronic mail (e-mail) transmission, or a posting of a data entry in a computer record relating to the patient, is a further aspect of the present invention.

BRIEF DESCRIPTION OF THE DRAWINGS

FIG. 1 is a schematic representation of the hierarchy of p53 diagnosis as provided by the invention; and FIG. 2 outlines two methods of immunoassay for the presence of anti-p53 antibodies in patient sera.

DETAILED DESCRIPTION OF THE INVENTION

The present invention relates to a method for the identification of p53 mutations, a method for generating reports for providing counseling to patients and families of patients with p53 mutations, and to oligonucleotide primers and kits useful in practicing these methods. The present invention utilizes the hierarchical approach which is disclosed generally in U.S. patent application Ser. No. 08/271,946, and in a concurrently filed continuation-in-part thereof, PCT/US95/08606, which is incorporated herein by reference.

The method for identification of p53 mutations in a sample of patients is based upon using diagnostic tools 1) in a hierarchy of increasing accuracy and cost per tool; and 2) in which each tool is of extremely high specificity and detects essentially no false positives. A sample which exhibits a positive result establishes the presence of a p53 mutation and a patient report can be prepared on this basis. A sample which exhibits a negative result is thereafter subjected to a more costly, but more accurate test to determine if a mutation is present.

Thus, as shown in FIG. 1, an example of such a hierarchy comprises, in order, an immunoassay step; a DNA fragment length/quantity analysis; and DNA sequencing. In the exemplary results shown in FIG. 1, the first step has the advantage of low cost, but detects a positive result in only 15% of the patients. The second level of the test hierarchy is of moderate cost, but because of its increased accuracy it detects a positive result in 30% (26 of 85) of the patients who tested negative using the immunoassay. This means that the more expensive DNA Sequencing analysis need only be performed on 59% of the original patients. Thus, the use of the hierarchical approach leads to a substantial reduction in the average cost of the test while providing high levels of accuracy for every patient, by having eliminated from the test pool those samples that are known to be positive.

IMMUNOASSAY PROCEDURES

As illustrated in FIG. 1, the first level in the hierarchy of p53 diagnosis may be an immunoassay. Because of the relatively low cost of immunoassay, it may be advantageously used to eliminate a significant number of patients from the sample pool prior to proceeding to the next level of the hierarchy. Methods of immunoassay that can be employed at this first stage have been discovered by many researchers. The following list of papers all include methods for identifying p53 mutations by immunoassay, though by no means is this list exclusive, and a practitioner skilled in the art may know of alternative methods of p53 immunoassay:

Angelopoulou et al., "Autoantibodies against the p53 tumor suppressor gene product quantified in cancer patient serum with time-resolved immunofluorometry", *Cancer J* 6(6): 315–321 (1993).

Bartek et al., *Oncogene* 6: 1699–1703 (1991).

Crawford et al., "Detection of antibodies against the cellular protein p53 in sera from patients with breast cancer", *Int J Cancer* 30: 403–8 (1982).

Caron De Froentel et al., "Presence of circulating antibodies against cellular protein p53 in a notable proportion of children with B-cell lymphoma", *Int J Cancer* 39: 185–9 (1987).

Christopoulos et al., "Oncogenes and tumor suppressor genes: new biochemical tests." *CRC Crit Rev Clin Lab Sci* 29: 269–305 (1992).

Davidoff et al., "Immune response to p53 is dependent upon p53 HSP70 complexes in breast cancers", *Proc Natl Acad Sci USA* 89: 3439–42 (1992).

Hassapoglidou et al., "Antibodies to the p53 tumor suppressor gene product quantified in cancer patient serum with a time-resolved immunofluorometric technique", *Clin Biochem* 25:445–9 (1992).

Hassapoglidou et al., "Quantification of p53 protein in tumor cell lines, breast tissue extracts and serum with time-resolved immunofluorometry", *Oncogene* 8:1501–1509 (1993).

Labrecque et al., "Analysis of the anti-p53 antibody response in cancer patients", *Cancer Res* 53: 3468–71 (1993).

Schlichtholz et al., "The immune response to p53 in breast cancer patients is directed against immunodominant epitopes unrelated to the mutational hot spot", *Cancer Res* 52: 6380–84 (1992).

Volkmann et al., "The humoral immune response to p53 in patients with hepatocellular carcinoma is specific for malignancy and independent of the alpha-fetoprotein status", *Hepatology* 18: 559–565 (1993).

Winter et al., "Development of antibodies against p53 in lung cancer patients appears to be dependent on the p53 mutation", *Cancer Res* 52: 4168–74 (1992).

In selecting an immunoassay for use in the present method, it should be understood that some immunoassays only detect small subsets of p53 mutations, while other immunoassays can detect a wide variety of p53 mutations. In order to reduce the cost of diagnosis, it is advantageous to take into account the scope of detection of each immunoassay and select an immunoassay which provides highly specific detection for the greatest number of p53 mutations as the analytical start point. If desired, a second immunoassay may be used after the first immunoassay if it will identify other types of mutations not found by the first immunoassay. This selection and sequential ordering of immunoassays may continue until the patient pool is reduced to eliminate essentially all patients reasonably diagnosed with immunoassay techniques before going on to other, more expensive and more accurate assays.

DNA ANALYSIS

The next level in the hierarchy of this invention test those patient samples which did not prove positive for p53 mutation based on immunoassay, be subjected to more accurate and more costly analysis. DNA analysis of patient samples is an non-limiting example of such an analysis. Within the general class of DNA analysis, however, there is a hierarchy of methods, each level in the hierarchy providing increasing accuracy but at increased cost. At the top end of this hierarchy (most accurate and expensive) is DNA sequencing. DNA sequencing provides the maximum degree of accuracy because each base in DNA from the sample is identified and compared to the wild-type sequence.

DNA analysis also provides the option of methods which are lower in the hierarchy than DNA sequencing but which offer greater accuracy than immunoassay procedures. A non-limiting example of such a test is an assay for DNA fragment length/quantity mutations. This fragment analysis can be used as an intermediate level in a three (or more) level hierarchy, or it can be used as the first level of a hierarchy in place of the immunoassay tests described above.

FRAGMENT ANALYSIS

As illustrated in FIG. 1, level two of the hierarchy of this invention may be DNA fragment length/quantity analysis. In this test, one or more exons of the p53 gene are quantitatively amplified using primers designed to create amplification products of known length and the lengths and/or quantity of the amplified fragments are determined. If there is a variance between the length of any amplified exon, and the normal length of that exon, this is an indication of an insertion or deletion mutation in that exon. The quantity of amplified material from amplification of a sample exon may also reflect the loss of genetic material. In particular, by comparing the quantity of amplified materials produced to standards amplified from a null allele (0 copies of p53), a hemizygous standard (1 copy of p53), a wild type standard (2 copies of p53) and a trisomy standard (3 copies of p53), the nature of the mutation may be further investigated.

The number of exons tested in step two of the hierarchy is a matter of choice for the user. For example, if after repeated testing on patient samples it is found that length or quantity mutations are rarely found in certain exons, it is preferable to test these exons last, after testing other exons to see if a mutation sufficient to cause the disease is detected, before incurring the expense to test these less likely exons. In testing these other exons, the user may choose to test them one at a time, or in one multiplexing group at a time. Alternatively, the user may choose to test all exons simultaneously at once.

When a length mutation is detected in this step of the hierarchy, it is not necessary to perform additional tests on the patient sample to complete the identification process. Preferably, however, the sequence of the mutated exon will be determined as part of the second level of the hierarchy to confirm that the mutation detected can in fact be a cause of the observed disease.

Again, all those samples that prove positive for a length or quantity mutation are eliminated from the patient sample, and patient reports may be made for each patient eliminated. However, if no mutation is detected at this level of the hierarchy, then a more accurate and costly analysis must be undertaken. DNA sequence analysis is a non-limiting example of such a level.

The primers used to amplify the sample DNA for fragment analysis are oligonucleotides of defined sequence selected to hybridize selectively with particular portions of the p53 gene, generally introns. Each primer has bound to it a detectable label. A preferred example of such a label is fluorescein, which is a standard label used in nucleic acid sequencing systems using laser light as a detection system. Other detectable labels can also be employed, however, including other fluorophores, radio-labels, chemical couplers such as biotin which can be detected with streptavidin-linked enzymes, and epitope tags such as digoxigenin detected using antibodies available from Boehringer-Mannheim.

While considerable variation is possible in the sequence of the primers used in amplifying the exons as part of the method of the present invention, the primers used in amplification and the conditions of the amplification are preferably optimized for use in the present invention. Looking first at the primers used, it will be understood that in order to avoid the possibility of false positive results the primer pair, i.e., the combination of the 5'-primer and the 3'-primer for any given exon must be unique to the p53 so that only the p53 gene will be amplified. This means that the primer sequences will be generally somewhat longer than the minimum which can be used as an amplification primer. Preferred primers are from 18 to 23 nucleotides in length, without internal homology or primer—primer homology. It is also desirable for the primers to form more stable duplexes with the target DNA at the primers' 5'-ends than at their 3'-ends, because this leads to less false priming. Stability can be approximated by GC content, since GC base pairs are more stable than AT pairs, or by nearest neighbor thermodynamic parameters. Breslauer et al., "Predicting DNA duplex stability from base sequence", *Proc. Nat'l Acad. Sci. USA* 83: 3746–3750 (1986). In addition, to ensure complete amplification of each exon, the two primers of a pair are preferably selected to hybridize in the introns immediately flanking the exon to be amplified using the primer pair.

Additional factors apply to the selection of primers for multiplexed amplification of exons, i.e., where several exons are amplified concurrently in a single reaction mixture. These factors are discussed in Rylchik, W., "Selection of Primers for Polymerase Chain Reaction", in *Methods in Molecular Biology, Vol.* 15: *PCR Protocols: Current Methods and Applications,* White, B. A. ed., Humana Press, Totowa, N.J., 1993. Briefly, applying these factors, primer pairs are selected by position, similarity of melting temperature, internal stability, absence of internal homology or homology to each other, i.e., they won't stick to each other or to themselves, and the 3'-end will not form a stable hairpin loop back on itself.

Thus, in the present case, the goal is to have sets of primer pairs with approximately the same thermal profile, so that they can be effectively coamplified together. This goal can be achieved by having groups of primer pairs with approximately the same length and the same G/C content. In addition, it is preferred that the length of the gene region between the primer binding sites on a normal p53 gene differ for each exon to be multiplexed as a group. Differences of only one base in length are sufficient, provided a high resolution gel capable of resolving one base differences is used in analyzing the amplification products. However, greater differences in length are preferred.

To evaluate compatibility of primers for use in coamplification, it is desirable to determine the predicted melting temperature for each primer. This can be accomplished in several ways. For example, the melting temperature, Tm can be calculated using either of the following equations:

$$Tm\ (°\ C.)=81.5+16.6\times\log\ [Na]+0.41\times(\%GC)-675/\text{length}$$

where [Na] is the concentration of sodium ions, and the %GC is in number percent, or $$Tm\ (°\ C.)=2\times(A+T)+4\times(G+C)$$

where A, T, G, and C represent the number of adenosine, thymidine, guanosine and cytosine residues in the primer. In general, primers for coamplification should be selected to have predicted melting temperatures differing by less than 4° C.

DNA SEQUENCE ANALYSIS

FIG. 1 illustrates that the final element of the hierarchy of p53 diagnosis is DNA sequencing. DNA sequence analysis involves determining the sequence of the exons to locate the mutation.

Sequencing is expensive and so it may be desirable to use a sub-hierarchy within this level of testing to reduce the likelihood of having to sequence all of the exons. In this case a suitable sub-hierarchy will be determined by identifying those exons wherein mutations are most likely to occur. Mutational hotspots have been identified at codons 175, 245, 248, 249, 273 and 282, which correspond to exon 5 for the first listed hotspot, exon 6 for the second three listed hotspots and exon 7 for the latter two hotspots. (Harris CC. p53: At the Crossroads of Molecular Carcino-genesis and Risk Assessment. *Science* 1993; 262: 1980–1981.) In accordance with this sub-hierarchy, the first exons sequenced are those which are easy to sequence and which contain hotspots. Next, if no mutation is found, hotspot exons are sequenced which are hard to sequence (i.e. are found empirically to give less clear results when treated similarly to other exons). Finally, the remaining exons are sequenced in descending order of the odds of finding a mutation based on prior epidemiological studies. (The order of sequencing of the exons may change as patient data accumulates on the location of point mutation hotspots.) If no mutation has been detected after all the exons have been sequenced, then it is concluded that there is no mutation in the test sample and a report is generated accordingly.

A preferred method for DNA sequencing as part of the method of the invention involves amplifying the exon of interest and then determining its sequence. Amplification of each exon may be performed using the same primers employed for fragment length analysis, although the detectable label included for the fragment analysis is not necessary for amplification prior to sequencing. In this case, however, multiplexed amplification cannot be used since only a single amplification product is desired.

The determination of the sequence of the amplified material may be carried out in any manner. A preferred approach, however, is the well-known Sanger method involving a template-dependent primer extension reaction in the presence of dideoxy chain terminating nucleotides. For this method, a sequencing primer is used which hybridizes to one chain of the amplified DNA. In general, sequencing primers are nested inside the amplification primers, although the amplification primers could be used for sequencing purposes if desired.

The amplification and sequencing primers used in the present invention are advantageously packaged as kits for the detection of mutations in the p53 gene. The primers may be packaged individually within the kit, or as mixtures of primers, sometimes referred to as "primer cocktails," which are useful in a single reaction vessel. Such kits may contain a single pair of primers, useful for quantitative amplification of a single exon, or multiple pairs of primers useful for amplification of multiple exons. Such kits may further include amplification and/or sequencing primers for one or more exons. Such kits may also include reagents other than primers for use in the amplification reaction, such as a polymerase and buffers, but this is optional.

Preferred kits in accordance with the invention comprise a plurality of primer pairs useful in the co-amplification of a plurality of exons of the p53 gene. Primer pairs in such kits are selected to have a common melting temperature and to produce amplification products having differing lengths.

The following non-limiting examples illustrate applications of the invention.

EXAMPLE 1

In order to determine the presence or absence of p53 mutations in a sample of patients, the following hierarchy of tests was performed.

Level 1

Immunoassay: Detection of anti-p53 antibodies

The two methods of Angelopoulou and Diamandis (1993, supra) were employed to detect anti-p53 antibodies in a patient sample. FIG. 2 A illustrates the principle of Method A for anti-p53 antibody quantification in patient sera. In the presence of such antibodies, a "sandwich" is formed between a mouse monoclonal anti-p53 antibody and human anti-p53 antibodies, resulting in high fluorescence readings. FIG. 2 B illustrates the principle of Method B for p53 antibody quantification in patient sera. The left-hand panel shows that in the absence of anti-p53 antibodies in human serum, the added p53 antigen is measured as shown, giving rise to fluorescence. The right-hand panel shows that when anti-p53 antibodies are present in patient serum, they block the added p53 antigen, resulting in low fluorescence. No sandwich can be formed between the mouse monoclonal and rabbit polyclonal anti-p53 antibodies. ALP=alkaline phosphatase; FSAP=fluorosalicyl phosphate; FSA= fluorosalicylate; Ab=antibody.

Instrumentation and Materials—For measuring liquid-phase Tb3+ fluorescence in white microtiter wells, a Cyberfluor 615 Immunoanalyzer time resolved fluorometer was used as described elsewhere (Christopoulous et al., supra; Papanastasiou-Diamandi et al., "Ultrasensitive thyrotropin immunoassay based on enzymatically amplified time-resolved fluorescence with a terbium chelate", *Clin Chem* 38:545–48 (1992)). The phosphate ester of 5-fluorosalicylic acid (FSAP) was obtained from CyberFluor Inc., Toronto, Canada. TbCl3. 6H20 was from GfS Chemicals, Columbus Ohio, USA. All other chemicals were form Sigma Chemical Co., St. Louis, Mo., USA unless otherwise stated.

Solutions—The enzyme substrate buffer was a 0.1 mol/L Tris solution, pH 9.1, containing 0.1 mol NaCl and 1 mmol $MgCl_2$ per liter. The stock FSAP substrate solution was a $10^{-2}$ mol/L solution in 0.1 mol/L NaOH. Fresh FSAP substrate working solutions were prepared just before use by dilution (10-fold) of the stock in the enzyme substrate buffer. The cell lysis buffer was a 20 mmol/L Tris solution, pH 8.1, containing 150 mmol NaCl, 10 g Nonidet P-40, 0.5 mmol phenylmethylsulfonyl fluoride, 2 mg leupeptin and 2 mg aprotinin per liter. The developing solution was a 1 mol/L Tris base solution containing 0.4 mol NaOH, 3 mmol EDTA and 2 mmol $TbCl_3.6H_2O$ per liter (no pH adjustment). The washing solution was a 5 mmol/L Tris buffer, pH 7.80, containing 0.5 g Tween 20 and 150 mmol NaCl per liter. The coating antibody solution was a 50 mmol/L Tris buffer, pH 7.80, containing 0.5 g sodium azide per liter. The CM-1 antibody diluent was a 50 mmol/l Tris buffer, pH 7.80. containing 60 g bovine serum albumin (BSA) per liter. The goat anti-rabbit immunoglobulin alkaline phosphatase conjugate (GARRIg-ALP) diluent was a 50 mmol/l Tris buffer, pH 7.80, containing 60g BSA, 0.5 mol KCl and 100 ml goat serum per liter.

The cell lines used in this study were colon carcinoma Colo 320 HSR(+) (Murakami et al., "Detection of aberrations of the p53 alleles and the gene transcript in human tumor cell lines by single-strand conformation polymorphism analysis", *Cancer Res* 51: 3356–61 (1991)); pancreatic carcinoma MIA PaCa-2 (Barton et al. "Abnormalities of the p53 tumor suppressor gene in human pancreatic cancer", *Br J Cancer* 64:1076–82 1991)); breast carcinoma T-47D (Bartek et al., "Genetic and immunochemical analysis of mutant p53 in human breast cancer cell lines", *Oncogene* 5:893–9 (1990)); and human erythroleukemia OCI M2 (Singerland et al., "Mutations of the p53 gene in human acute myelogenous leukemia", *Blood* 77: 1500–7 (1991)).

These cell lines were cultured as described elsewhere; they all have p53 gene mutations and overproduce mutant p53 protein (Hassapoglidou et al., 1993, supra). Recombinant wild type p53 protein, produced as described elsewhere (Wang et al., "The murine p53 blocks replication of SV40 DNA in vitro by inhibiting the initiation functions of SV40 large T antigen", *Cell* 57: 379–92 (1989)), was a gift by Dr. Carol Prives, Columbia University, N.Y.

Lysates from cell lines producing p53, or recombinant p53 were diluted in a 50 mmol/L Tris buffer, pH 7.80, containing 60 g of BSA per liter for Method A and in 100% goat serum for Method B. The mouse monoclonal anti-p53 capture antibody (Pab240) diluent was a 50 mmol/L Tris buffer, pH 7.80, containing 60 g BSA and 0.5 mol KCl per liter. Serum samples were diluted in a serum diluent which is the same as the Pab240 diluent but supplemented with 10% normal goat serum and 2% normal mouse serum. The goat anti-human immunoglobulin-alkaline phosphatase conjugate (GAHIg-AALP) diluent was the same as the GARIg-ALP diluent.

The mouse anti-p53 monoclonal antibody Pab240 was produced as a tissue culture supernatant from a cell line donated to us by Dr. D. P. Lane, University of Dundee, U.K. Its antibody concentration was approximately 30 micrograms/ml. The rabbit polyclonal anti-p53 antibody, CM-1, was obtained from Dimension Labs, Mississauga Ontario. The goat anti-rabbit and goat anti-human antibodies, conjugated to alkaline phosphatase, and the goat anti-mouse antibody, Fc fragment specific (GAMIg), all approximately 1 mg/ml, were obtained from Jackson Imunoresearch, West Grove, Pa.

Patient Sera—Sera from cancer patients were stored at −70° C. until analysis. Sera used were from patients with breast (n=105), ovarian (n=72), colon (n=77) and pancreatic cancer (n=46). For correlation studies 38 p53 antibody-positive sera from patients with the above malignancies was used plus sera from prostate, lymphoma, lung and multiple myeloma patients.

Procedures

Cell Lysis—Cells from each cell line were grown until they reached approximately 10×6 cells/ml or 90% confluency. The cell pellet from a 15 ml culture was lysed in 300 microliters lysis buffer, for 30 min, on ice. The cell extract was centrifuged at 12,000×g for 10 min and the pellet discarded. The lysate was used within two hours. Total protein was measured in the lysates with the bicinchoninic acid (BCA) assay, commercially available from Pierce Chemical Co., Rockford Ill. Lysates typically contained 1–3 mg of protein per ml.

Immunoassay Procedure, Method A—This method is a modification of an assay previously published (Hassapoglidou 1992, supra). White, opaque, 12-well microtiter strips (from Dynatech laboratories, Alexandria, Va.) were coated with goat anti-mouse immunoglobulin diluted 500-fold in the coating antibody diluent (100 microliters/ 200 ng/well, overnight incubation at room temperature). This indirect coating is superior to direct coating with the Pab240 antibody. The wells were then washed six times with an automatic washer and used for the assay as follows: 50 microliters of cell lysate (diluted 10-fold in the cell lysate diluent) and 100 microliters of mouse monoclonal anti-p53 antibody Pab240 (diluted 20-fold in the PAb240 diluent) were added and incubated for 3 h with shaking at 37 C (air oven). After 6 washes, 100 microliter/well of serum sample (diluted 10-fold in the serum sample diluent, in duplicate) and incubate for 1 h with shaking, at room temperature. After six washes, 100 microliters/well of an alkaline phosphatase-labeled goat anti-human immunoglobulin G-antibody (diluted 15,000 fold in the GAHIg-ALP diluent) was added. The wells were incubated for 1 h with shaking at room temperature and washed six times. 100 microliters/well of the diluted FSAP substrate solution was added and incubated for 10 min with shaking at room temperature. 100 microliters/well of the developing solution, was added, mixed for 1 min and the fluorescence was measured on a Cyberfluor 615TM immunoanalyzer.

Each assay run was accompanied by a parallel run to assess any nonspecific binding effects. This run was identical to the procedure described above but the cell lysate was replaced by the lysate diluent. Sera were considered positive for antibodies only if the signal with the lysate exceed the signal without the lysate by a factor of 1.7 (Hassapoglidou 1992, supra).

Immunoassay Procedure Method B—Microtiter strips were coated as in Method A. Patient serum (200 microliters) was then incubated in tubes with 20 microliters of a 10-fold diluted cell lysate from Colo 320 HSR (+) cells, for 30 min at room temperature. The p53-supplemented sera (50 microliters, in duplicate) were then added to goat anti-mouse IgG-coated wells along with 100 microliters/well of mouse monoclonal anti-p53 antibody Pab240, diluted 20 fold as in Method A. The wells were incubated at 37 C for 3 h with shaking and washed six times. 100 microliters/well of the rabbit anti-p53 polyclonal antibody (CM-1) diluted 5,000 fold in the CM-1 antibody diluent was added and incubated for 1 h at room temperature with shaking. After washing six times 100 microliters/well of the alkaline phosphatase-labeled goat anti-rabbit immunoglobulin (GARIg-ALP)

diluted 5000-fold in the GARIg-ALPP antibody diluent was added and incubated for 1 h at room temperature with shaking. The wells were washed six times and the procedure continued as in Method A from the point of adding the FSAP substrate solution. Each serum sample was also assayed without the addition of the Colo 320 HSR(+) cell lysate to assess the background signal. Sera were considered positive for antibodies only if the fluorescence signal in the presence of serum was less than 50% of the fluorescence signal obtained with a 6% BSA solution as sample.

Quantification—Due to the lack of a suitable standard solution, an arbitrary system to calibrate Methods A and B was devised. Among the highly p53 antibody-positive sera one was selected and arbitrarily defined to have a concentration of 20,480 Units/L. This serum sample as then used in dilutions to construct calibration curves for assays A and B from which the concentration of the other samples was calculated.

The results of the test identified the presence of anti-p53 antibodies in 15–16% of ovarian and colon cancer patients. Antibody prevalence was between 5–8% in patients with lung and breast tumors. There was a relatively low prevalence of detectable anti-p53 antibodies (3–4%) in patients with pancreatic and prostate cancer and in patients with multiple myeloma or lymphoma. In patients with other malignancies (hepatoma, melanoma, leukemia, Kaposi's sarcoma and testicular carcinoma) the p53-antibody prevalence was similar to that of non-cancer patients (less than 2%).

Patient reports were prepared for those samples which demonstrated positive results. All those test samples which were not positive for the p53 mutation in the protein immunoassay were then analyzed at the next level in the hierarchy of the invention.

Level 2

DNA Fragment Length/Quantity Analysis

DNA is prepared from the patient sample using a Qiagen QIAamp Kit according to accompanying directions. Briefly, an aliquot of the blood sample, or a lymphocyte—containing fraction thereof, is combined with Proteinase K, mixed, and allowed to incubate to lyse the cells. Ethanol is added and the lysate is transferred to a QIAamp spin column from which DNA is recovered after several washings.

Quantitative fragment length and amount analysis is performed to assay for 1) the presence of insertion or deletion mutations; and 2) whether the patient is homozygous or heterozygous for the insertion or deletion mutation. To perform the analysis, the genomic DNA is amplified in three sets using multiplexing amplification primers. Each 50 microliter multiplexed PCR reaction contains 0.5 micrograms genomic DNA, 150 ng or each primer, 3.6 mM each dNTP, 42.5 micrograms Bovine Serum Albumin, 5 units Taq polymerase in a buffer containing 10% DMSO, 16 mM $(NH_4)_2SO_4$, 6.7 mM $MgCl_2$, 6.8 micro Molar EDTA (pH 8.0) and 1 mM β-mercaptoethanol. The reaction mixture was initially incubated at 94 degrees C for 5 minutes and then subjected to 30 cycles of PCR in a Perkin-Elmer/Cetus thermocycler as follows:

Denaturation: 94 degrees C, 30 seconds

Annealing: 60, 62 or 64 degrees C (depending on whether primer set A, B, or C is being amplified, respectively) for 50 secs.

Extension: 70 degrees C, 60 seconds; final extension at 72 degrees for 3 minutes The amplification of the eleven exons of the p53 gene is advantageously carried out in three multiplex pools. In multiplex pool A, exons 1, 3, 4, 5, 6, 9, 10 and 11 are amplified (along with a control sequence). The members of this pool are selected because they all use a hybridization temperature of 60° C., and none of the expected fragment lengths will overlap in an electrophoresis gel. One of each pair of primers is labeled at the 5 prime end with an identifiable marker such as fluorescein, rhodamine or cyanine. The primers are:

| EXON 1 | | |
|---|---|---|
| P53-5X1MP CGGATTACTT GCCCTTACTT GTCA | [SEQ 1] | |
| P53-3X1MP CCCCAGCCCC AGCGATTTT | [SEQ 2] | |
| EXON 3 | | |
| P53-5X3,4P CATGGGACTG ACTTTCTGCT | [SEQ 3] | |
| P53-3X3MP CCACGGCAAC GCCCACTGT | [SEQ 4] | |
| EXON 4 | | |
| P53-5X4MP CTGCTCCTCT CACTGCTCTT TTCA | [SEQ 5] | |
| P53-3X3,4P AAAGAAATCC AGCCCGATAC CG | [SEQ 6] | |
| EXON 5 | | |
| P53-5X5, 6P TGTTCACTTC TCCCCTGACT | [SEQ 7] | |
| P53-3X5MP CACCCCTCTC CTCTCTCCAC | [SEQ 8] | |
| EXON 6 | | |
| P53-5X6MP CTGGCGCTGG AGAGACGACA | [SEQ 9] | |
| P53-3X5,6P GCAGCCCCAC TGACAACCA | [SEQ 10] | |
| EXON 9 | | |
| P53-5X9P GCGGTCGAGC AGACCAACG | [SEQ 11] | |
| P53-3X9P AACGCCATTT TCAGTGTTAC A C | [SEQ 12] | |
| EXON 10 | | |
| P53-5X10P TCATCCCTCA TAAACTCAAA CAA | [SEQ 13] | |
| P53-3X10P CTCGACGCAA CAATCTCCTT A | [SEQ 14] | |
| EXON 11 | | |
| P53-5X11P GCCACAGACC CTCTCACTCA T | [SEQ 15] | |
| P53-3X11P TGCTTCTGAC GCACACCTAT T | [SEQ 16] | |

These primers result in amplified products with normal fragment lengths of 331 bp for exon 1, 162 bp for exon 3, 382 bp for exon 4, 268 bp for exon 5, 247 bp for exon 6, 209 bp for exon 9, 390 bp for exon 10, and 256 bp for exon 11. The control sequence produces a further fragment having a length which should not correspond to any of the expected lengths.

In multiplex pool B, exons 2 and 8 are amplified (along with a control sequence). The members of this pool are selected because they all use a hybridization temperature of 62° C., and none of the expected fragment lengths will overlap in an electrophoresis gel. One of each pair of primers is labeled at the 5 prime end with an identifiable marker such as fluorescein, rhodamine or cyanine. The primers are:

| EXON 2 | | |
|---|---|---|
| P53-5X2P | | |
| ACCCAGGGTT GGAAGCGTCT | [SEQ 17] | |
| P53-3X2P | | |
| GACAAGAGCA GAAAGTCAGT CC | [SEQ 18] | |
| EXON 8 | | |
| P53-5X8P | | |
| GACAAGGGTG GTTGGGAGTA GATG | [SEQ 19] | |
| P53-3X8P | | |
| GCAAGGAAAG GTGATAAAAG TGAA | [SEQ 20] | |

These primers result in amplified products with normal fragment lengths of 261 bp for exon 2 and 320 bp for exon 8. The control sequence produces a further fragment having a length which should not correspond to any of the expected lengths.

Finally, in multiplex pool C, only exon 7 is amplified (along with a control sequence). The primers for exon 7 require a hybridization temperature of 64° C. unlike any of the other amplification primers. One of the pair of primers is labeled at the 5 prime end with an identifiable marker such as fluorescein, rhodamine or cyanine. The primers are:

| EXON 7 | |
|---|---|
| P53-5X7P | |
| GGCGACAGAG CGAGATTCCA | [SEQ 21] |
| P53-3X7P | |
| GGGTCAGCGG CAAGCAGAGG | [SEQ 22] |

These primers result in an amplified product with a normal fragment length of 286 bp. The control sequence produces a further fragment having a length which should not correspond to this expected length.

After amplification, the products from each amplification reaction are denatured and loaded into a polyacrylamide gel for electrophoretic separation. In the preferred embodiment, electrophoretic separation takes place in a semi-automated electrophoresis apparatus such as in a Pharmacia A.L.F.™ automated sequencer. In another embodiment, electrophoretic separation takes place in a microgel disclosed in U.S. patent application Ser. No. 08/332,577, which is incorporated herein by reference. In either embodiment, the amplification products migrate through the gel at a rate determined by their length and are detected using the fluorescence of the fluorescent molecule (either fluorescein, rhodamine or cyanine) which was attached to the primers.

The products of each amplification set are separated in a different lane of the gel, unless molecules which fluoresce at different wavelengths have been used as labels on the primers, in which case the products may be run in the same lane, and distinguished by wavelength of fluorescence emission. The fragment sizes and amounts are compared to the expected sizes of the normal gene fragments. If length mutation is detected, then the sample is concluded to contain a mutation in the p53 gene. If the amount of amplified fragment is 25% or more below or above the amount of the wild type fragment (using the amount of control fragment as a standard of comparison), then the sample is concluded to contain an LOH (loss of heterozygosity) or gene amplification mutation, respectively. A patient report was prepared for those samples that are identified as having a fragment length or quantity mutation. Where no length or quantity mutation is detected, then the sample was re-examined using the next and final level of the hierarchy.

Level 3

DNA Sequence Analysis

The group of patient samples that have proven negative for p53 mutations under the protein immunoassay and the fragment length/quantity analysis may be re-examined for point mutations in the DNA sequence.

DNA from an individual patient is purified as in the fragment length/quantity analysis, above. Exon containing fragments of the p53 gene are amplified using primers and conditions listed in Table 1. The primers are the same as those used in the fragment length/quantity analysis. However, in some cases the primers are used in different combinations. For example, because exons 5 and 6 lie in reasonably close proximity on genomic DNA, it is adequate for amplification to use the primer at the 5 prime end of exon 5 and at the 3 prime end of exon 6, and to amplify both exons together on a single fragment. The resulting amplified fragment is suitable for sequencing either exon 5 or exon 6. The same situation is found with exons 3 and 4.

TABLE 1

PRE-SEQUENCING AMPLIFICATION CONDITIONS

| EXON | 5' primer | 3' primer | initial denaturing temp/time | denaturing temp/time | anneal temp/time | Extension temp/time | cycles | final extension temp/time |
|---|---|---|---|---|---|---|---|---|
| 1 | p53-5X1PCR | p53-3X1PCR | 94° C./4 min | 94° C./30 min | 60° C./50 min | 70° C./60 min | 30 | 72° C./3 min 72° C./3 min |
| 2 | p53-5X2PCR | p53-3X2PCR | 94° C./4 min | 94° C./30 min | 62° C./50 min | 70° C./60 min | 30 | 72° C./3 min |
| 3 | p53-5X3PCR | p53-3X3PCR | 94° C./4 min | 94° C./30 min | 60° C./50 min | 70° C./60 min | 30 | 72° C./3 min |
| 4 | p53-5X4PCR | p53-3X4PCR | 94° C./4 min | 94° C./30 min | 60° C./50 min | 70° C./60 min | 30 | 72° C./3 min |
| 5 | p53-5X5PCR | p53-3X5PCR | 94° C./4 min | 94° C./30 min | 60° C./50 min | 70° C./60 min | 30 | 72° C./3 min |
| 6 | p53-5X6PCR | p53-3X6PCR | 94° C./4 min | 94° C./30 min | 60° C./50 min | 70° C./60 min | 30 | 72° C./3 min |
| 7 | p53-5X7PCR | p53-3X7PCR | 94° C./4 min | 94° C./30 min | 64° C./50 min | 70° C./60 min | 30 | 72° C./3 min |
| 8 | p53-5X8PCR | p53-3X8PCR | 94° C./4 min | 94° C./30 min | 62° C./50 min | 70° C./60 min | 30 | 72° C./3 min |
| 9 | p53-5X9PCR | p53-3X9PCR | 94° C./4 min | 94° C./30 min | 60° C./50 min | 70° C./60 min | 30 | 72° C./3 min |
| 10 | p53-5X10PCR | p53-3X10PCR | 94° C./4 min | 94° C./30 min | 60° C./50 min | 70° C./60 min | 30 | 72° C./3 min |
| 11 | p53-5X11PCR | p53-3X10PCR | 94° C./4 min | 94° C./30 min | 60° C./50 min | 70° C./60 min | 30 | 72° C./3 min |

Once the sets of exons are amplified, DNA sequencing reactions may be performed on the amplified sample. Dideoxy sequencing primers have been developed for both strands of each exon (except exon 3 which has only one sequencing primer) of the p53 gene, and are listed below:

| | |
|---|---|
| EXON 1 | |
| P53-5X1SEQ CCCATTACTT CCCCTTACTT CTCA* | [SEQ 1] |
| P53-3X1SEQ CCCCACCCCC ACCCATTTT | [SEQ 2] |
| EXON 2 | |
| P53-5X2SEQ CCACCCTTCC AACCCTCTC* | [SEQ 23] |
| P53-3X2SEQ GCTACCCCGC TCGGCTTGC | [SEQ 24] |
| EXON 3 | |
| P53-3X3SEQ ATGGCTCAAA ACACCACT* | [SEQ 25] |
| EXON 4 | |
| P53-5X4SEQ CGGCCTGAGG ACCTGCTC | [SEQ 26] |
| P53-3X4SEQ ATACCCCCAC GCATTCAA | [SEQ 27] |
| EXON 5 | |
| PS3-5X5SEQ CACTTCTCCC CTGACTTT* | [SEQ 28] |
| P53-3X5SEQ CCTCGGGACC CTCCGCAA | [SEQ 29] |
| EXON 6 | |
| P53-5X6SEQ TGGTTGCCCA CCCTCCCC* | [SEQ 30] |
| P53-3X6SEQ CCACTGACAA CCACCC | [SEQ 31] |
| EXON 7 | |
| P53-5X7SEQ CTCCCCTGCT TCCCACA* | [SEQ 32] |
| P53-3X7SEQ TCACCCCCAA CCACACC | [SEQ 33] |
| EXON 8 | |
| P53-5X8SEQ ATGCCACACG TACCACC* | [SEQ 34] |
| P53-3X8SEQ CATAACTGCA CCCTTCG | [SEQ 35] |
| EXON 9 | |
| P53-5X9SEQ GGAGGAGACC AAGGGTGC | [SEQ 36] |
| P53-3X9SEQ GGAAACTTTC CACTTGA* | [SEQ 37] |
| EXON 10 | |
| P53-5X10SEQ CCATCTTTTA ACTCAGGT* | [SEQ 38] |
| P53-3X10SEQ CATGAAGGCA GGATGAG | [SEQ 39] |
| EXON 11 | |
| P53-5X11SEQ AGACCCTCTC ACTCATG | [SEQ 40] |
| P53-3X11SEQ CAAGCAAGGG TTCAAAG* | [SEQ 41] |

The primers are generally nested inside the amplification primers, i.e. closer to the exon, although in some cases the preferred sequencing primer is in fact the amplification primer. The 5 prime sequencing primer provides the sequence from the sense strand; the 3 prime sequencing primer provides the sequence from the anti-sense strand of the p53 gene. Only one of these primers needs to be used to obtain sequence from the exon in question. The preferred primer is marked with an asterisk in the list above. The preferred primer for sequencing is conjugated to a fluorescent molecule such as fluorescein, rhodamine or cyanine for detection, although other forms of detectable labels, including labeled nucleotides or dideoxynucleotides may be employed.

Dideoxy DNA sequencing is performed using the well known method of Sanger et al., "DNA sequencing with chain terminating inhibitors", *Proc Natl Acad Sci USA* 74:5463–5467 (1977), as modified for use with Sequenase™ Version 2.0 (United States Biochemical Corporation, Cleveland Ohio) Products of the DNA sequencing reaction are analyzed using a semi-automated electrophoresis apparatus as in the DNA fragment length/quantity analysis described above.

Current epidemiological data was used to determine which gene fragments are preferably sequenced first. Mutations have been detected in all exons, but are extremely rare in exon 1 and in the 3'-end of exon 11. It is therefore preferable to sequence exons 2–10 ahead of exons 1 and 11. Currently the preferred order of sequencing begins with exon 6, then 7, then 5. The remaining exons are sequenced in turn.

Samples wherein mutations are detected relative to the wild-type p53 gene are recorded and reported to the individual patient's file. Where no mutation is identified, another exon containing fragment of the individual sample is sequenced. Again mutations are identified and reported. If, after sequencing all the exon containing fragments of the gene, there are no mutations identified, it is concluded that the individual sample contains no p53 mutation.

All final results of testing are reported to the patient file. The report is communicated to the patient by electronic transmission or written report, or both.

EXAMPLE 2

A second embodiment of the p53 assay skips the protein immunoassay level and begins with the preparation of DNA from a patient blood sample. Genomic DNA is prepared from a blood sample as in Example 1 and it is assayed according to the DNA measurement procedures of Example 1, including fragment length/quantity analysis and DNA sequence analysis. Patient reports are prepared when diagnosis of the presence or absence of p53 mutation is determined.

We claim:

1. A kit for the identification of mutations in the p53 gene, comprising at least one primer pair for amplification of an exon of the p53 gene, each member of said primer pair being labeled with a detectable label, wherein the kit comprises a primer pair selected from the group consisting of: 1

| | | |
|---|---|---|
| (a) | CGGATTACTT GCCCTTACTT GTCA | [SEQ 1] |
| and | CCCCAGCCCC AGCGATTTT | [SEQ 2]; |
| (b) | CATGGGACTG ACTTTCTGCT | [SEQ 3] |
| and | GGACGGCAAG GGGGACTGT | [SEQ 4]; |
| (c) | CTGGTCCTCT GACTGCTCTT TTCA | [SEQ 5] |
| and | AAAGAAATGC AGGGGGATAC GG | [SEQ 6]; |
| (d) | TGTTCACTTG TGCCCTGACT | [SEQ 7] |
| and | CAGCCCTGTC GTCTCTCCAG | [SEQ 8]; |
| (e) | CTGGGGCTGG AGAGACGACA | [SEQ 9] |
| and | GGAGGGCCAC TGACAACCA | [SEQ 10]; |
| (f) | GCGGTGGAGG AGACCAAGG | [SEQ 11] |
| and | AACGGCATTT TGAGTGTTAG A C | [SEQ 12]: |
| (g) | TGATCCGTCA TAAAGTCAAA CAA | [SEQ 13] |
| and | GTGGAGGCAA GAATGTGGTT A | [SEQ 14]; |
| (h) | GGCACAGACC CTCTCACTCA T | [SEQ 15] |
| and | TGCTTCTGAC GCACACCTAT T | [SEQ 16]; |
| (i) | ACCCAGGGTT GAAGCGTCT | [SEQ 17] |
| and | GACAAGAGCA GAAAGTCAGT CC | [SEQ 18]; |
| (j) | GACAAGGGTG GTTGGGAGTA GATG | [SEQ 19] |
| and | GCAAGGAAAG GTGATAAAAG TGAA | [SEQ 20]; and |
| (k) | GGCGACAGAG CGAGATTCCA | [SEQ 21] |
| and | GGGTCAGCGG CAAGCAGAGG | [SEQ 22]. |

2. A kit according to claim 1, further comprising at least one p53 sequencing primer for the exon.

3. A kit according to claim 2, wherein the sequencing primer is selected from the group consisting of

| | |
|---|---|
| CGGATTACTT GCCCTTACTT GTCA | [SEQ 1], |
| CCCCAGCCCC AGCGATTTT | [SEQ 2], |
| CCAGGGTTGG AAGCGTCTC | [SEQ 23], |
| GCTAGGGGGC TGGGGTTGG | [SEQ 24], |
| ATGGGTGAAA AGAGCAGT | [SEQ 25], |
| GGGGCTGAGG ACCTGGTC | [SEQ 261], |
| ATACGGCCAG GCATTGAA | [SEQ 27], |
| CACTTGTGCC CTGACTTT | [SEQ 28] |
| CCTGGGGACC CTGGGCAA | [SEQ 29], |
| TGGTTGCCCA GGGTCCCC | [SEQ 30], |
| CCACTGACAA CCACCC | [SEQ 31], |
| CTCCCCTGCT TGCCACA | [SEQ 321], |
| TCAGCGGCAA GCAGAGG | [SEQ 33], |
| ATGGGACAGG TAGGACC | [SEQ 34], |
| CATAACTGCA CCCTTGG | [SEQ 35], |
| GGAGGAGACC AAGGGTGC | [SEQ 36], |
| GGAAACTTTC CACTTGA | [SEQ 37], |
| CCATCTTTTA ACTCAGGT | [SEQ 38], |
| CATGAAGGCA GGATGAG | [SEQ 39], |
| AGACCCTCTC ACTCATG | [SEQ 40], and |
| CAAGCAAGGG TTCAAAG | [SEQ 41]. |

4. A kit according to claim 1, wherein the kit comprises at least one primer cocktail containing a mixture of primers effective to coamplify a plurality of exons of the p53 gene.

5. A kit according to claim 4, wherein the primer cocktail contains a mixture of primers effective to amplify exons 2 and 8 of the p53 gene.

6. A kit according to claim 5, wherein the primer cocktail comprises primers of the sequence:

| | |
|---|---|
| ACCCAGGGTT GGAAGCGTCT | [SEQ 17] |
| GACAAGAGCA GAAAGTCAGT CC | [SEQ 18] |
| GACAAGGGTG GTTGGGAGTA GATG | [SEQ 19] and |
| GCAAGGAAAG GTGATAAAAG TGAA | [SEQ 20]. |

7. A kit according to claim 5, wherein the primer cocktail contains a mixture of primers effective to amplify exons 1, 3, 4, 5, 6, 9 and 10 of the p53 gene.

8. A kit according to claim 7, wherein the primer cocktail comprises primers of the sequence:

| | |
|---|---|
| CGGATTACTT GCCCTTACTT GTCA | [SEQ 1] |
| CCCCAGCCCC AGCGATTTT | [SEQ 2] |
| CATGGGACTG ACTTTCTGCT | [SEQ 3] |
| GGACGGCAAG GGGGACTGT | [SEQ 4] |
| CTGGTCCTCT GACTGCTCTT TTCA | [SEQ 5] |
| AAAGAAATGC AGGGGGATAC GG | [SEQ 6] |
| TGTTCACTTG TGCCCTGACT | [SEQ 7] |
| CAGCCCTGTC GTCTCTCCAG | [SEQ 8] |
| CTGGGGCTGG AGAGACGACA | [SEQ 9] |
| GGAGGGCCAC TGACAACCA | [SEQ 10] |
| GCGGTGGAGG AGACCAAGG | [SEQ 11] |
| AACGGCATTT TGAGTGTTAG AC | [SEQ 12] |
| TGATCCGTCA TAAAGTCAAA CAA | [SEQ 13] |
| GTGGAGGCAA GAATGTdGTT A | [SEQ 14] |
| GGCACAGACC CTCTCACTCA T | [SEQ 15] and |
| TGCTTCTGAC GCACACCTAT T | [SEQ 16]. | to produce a reaction mixture and thermally cycling the reaction mixture to produce at least one species of amplified product.

9. A primer cocktail comprising a plurality of oligonucleotide primer pairs for amplification of exons of the p53 gene, including a first primer pair for amplification of only exon 2 and a second primer pair for amplification of only exon 8 of the p53 gene.

10. A primer cocktail comprising a plurality of oligonucleotide primers for amplification of exons 2 and 8 of the p53 gene, wherein the primer cocktail comprises primers of the sequence:

| | |
|---|---|
| ACCCAGGGTT GGAAGCGTCT | [SEQ 17] |
| GACAAGAGCA GAAAGTCAGT CC | [SEQ 18] |
| GACAAGGGTG GTTGGGAGTA GATG | [SEQ 19] and |
| GCAAGGAAAG GTGATAAAAG TGAA | [SEQ 20]. |

11. A primer cocktail comprising a plurality of oligonucleotide primer pairs for amplification of exons of the p53 gene, including separate primer pairs for amplification of each of exons 1, 3, 4, 5, 6, 9 and 10 of the p53 gene.

12. A primer cocktail comprising a plurality of oligonucleotide primers for amplification of exons 1, 3, 4, 5, 6, 9 and 10 of the p53 gene, wherein the primer cocktail comprises primers of the sequence:

| | |
|---|---|
| CGGATTACTT GCCCTTACTT GTCA | [SEQ 1] |
| CCCCAGCCCC AGCGATTTT | [SEQ 2] |
| CATGGGACTG ACTTTCTGCT | [SEQ 3] |
| GGACGGCAAG GGGGACTGT | [SEQ 4] |
| CTGGTCCTCT GACTGCTCTT TTCA | [SEQ 5] |
| AAAGAAATGC AGGGGGATAC GG | [SEQ 6] |
| TGTTCACTTG TGCCCTGACT | [SEQ 7] |
| CAGCCCTGTC GTCTCTCCAG | [SEQ 8] |

-continued

| | |
|---|---|
| CTGGGGCTGG AGAGACGACA | [SEQ 9] |
| GGAGGGCCAC TGACAACCA | [SEQ 10] |
| GCGGTGGAqG AGACCAAGG | [SEQ 11] |
| AACGGCATTT TGAGTGTTAG AC | [SEQ 12] |
| TGATCCGTCA TAAAGTCAAA CAA | [SEQ 13] |
| GTGGAGGCAA GAATGTGGTT A | [SEQ 14] |
| GGCACAGACC CTCTCACTCA T | [SEQ 15] and |
| TGCTTCTGAC GCACACCTAT T | [SEQ 16]. |

13. A kit according to claim 2, wherein the kit comprises at least one primer cocktail containing a mixture of primers effective to coamplify a plurality of exons of the p53 gene.

14. A kit according to claim 3, wherein the kit comprises at least one primer cocktail containing a mixture of primers effective to coamplify a plurality of exons of the p53 gene.

15. A method for amplification of at least one exon of the human p53 gene in a sample comprising the steps of combining the sample with at least one primer pair selected from the group consisting of:

| | | |
|---|---|---|
| (a) and | CGGATTACTT GCCCTTACTT GTCA | [SEQ 1] |
| | CCCCAGCCCC AGCGATTTT | [SEQ 2]; |
| (b) and | CATGGGACTG ACTTTCTGCT | [SEQ 3] |
| | GGACGGCAAG GGGGACTGT | [SEQ 4]; |
| (c) and | CTGGTCCTCT GACTGCTCTT TTCA | [SEQ 5] |
| | AAAGAAATGC AGGGGGATAC GG | [SEQ 6]; |
| (d) and | TGTTCACTTG TGCCCTGACT | [SEQ 7] |
| | CAGCCCTGTC GTCTCTCCAG | [SEQ 8]; |
| (e) and | CTGGGGCTGG AGAGACGACA | [SEQ 9] |
| | GGAGGGCCAC TGACAACCA | [SEQ 10]; |
| (f) and | GCGGTGGAGG AGACCAAGG | [SEQ 11] |
| | AACGGCATTT TGAGTGTTAG AC | [SEQ 12]; |
| (g) and | TGATCCGTCA TAAAGTCAAA CAA | [SEQ 13] |
| | GTGGAGGCAA GAATGTGGTT A | [SEQ 14]; |
| (h) and | GGCACAGACC CTCTCACTCA T | [SEQ 15] |
| | TGCTTCTGAC GCACACCTAT T | [SEQ 16]; |
| (i) and | ACCCAGGGTT GGAAGCGTCT | [SEQ 17] |
| | GACAAGAGCA GAAAGTCAGT CC | [SEQ 18]; |
| (j) and | GACAAGGGTG GTTGGGAGTA GATG | [SEQ 19] |
| | GCAAGGAAAG GTGATAAAAG TGAA | [SEQ 20]; and |
| (k) and | GGCGACAGAG CGAGATTCCA | [SEQ 21] |
| | GGGTCAGCGG CAAGCAGAGG | [SEQ 22]; |

16. The method according to claim 15, wherein sample is combined with at least one primer cocktail containing a mixture of primers effective to coamplify a plurality of exons of the p53 gene.

17. The method according to claim 16, wherein the primer cocktail contains a mixture of primers effective to amplify exons 2 and 8 of the p53 gene.

18. The method according to claim 17, wherein the primer cocktail comprises primers of the sequence:

| | |
|---|---|
| ACCCAGGGTT GGAAGCGTCT | [SEQ 17] |
| GACAAGAGCA GAAAGTCAGT CC | [SEQ 18] |
| GACAAGGGTG GTTGGGAGTA GATG | [SEQ 19] and |
| GCAAGGAAAG GTGATAAAAG TGAA | [SEQ 20]. |

19. The method according to claim 16, wherein the primer cocktail contains a mixture of primers effective to amplify exons 1, 3, 4, 5, 6, 9 and 10 of the p53 gene.

20. The method according to claim 19, wherein the primer cocktail comprises primers of the sequence:

| | |
|---|---|
| CGGATTACTT GCCCTTACTT GTCA | [SEQ 1] |
| CCCCAGCCCC AGCGATTTT | [SEQ 2] |
| CATGGGACTG ACTTTCTGCT | [SEQ 3] |
| GGACGGCAAG GGGGACTGT | [SEQ 4] |
| CTGGTCCTCT GACTGCTCTT TTCA | [SEQ 5] |
| AAAGAAATGC AGGGGGATAC GG | [SEQ 6] |
| TGTTCACTTG TGCCCTGACT | [SEQ 7] |
| CAGCCCTGTC GTCTCTCCAG | [SEQ 8] |
| CTGGGGCTGG AGAGACGACA | [SEQ 9] |
| GGAGGGCCAC TGACAACCA | [SEQ 10] |
| GCGGTGGAGG AGACCAAGG | [SEQ 11] |
| AACGGCATTT TGAGTGTTAG AC | [SEQ 12] |
| TGATCCGTCA TAAAGTCAAA CAA | [SEQ 13] |
| GTGGAGGCAA GAATGTGGTT A | [SEQ 14] |
| GGCACAGACC CTCTCACTCA T | [SEQ 15] and |
| TGCTTCTGAC GCACACCTAT T | [SEQ 16]. |

21. A method for sequencing a portion of a human p53 gene in a sample comprising the steps of combining the sample with a sequencing reaction mixture containing a sequencing primer selected from the group consisting of

| | |
|---|---|
| CGGATTACTT GCCCTTACTT GTCA | [SEQ 1], |
| CCCCAGCCCC AGCGATTTT | [SEQ 2], |
| CCAGGGTTGG AAGCGTCTC | [SEQ 23], |
| GCTAGGGGGC TGGGGTTGG | [SEQ 24], |
| ATGGGTGAAA AGAGCAGT | [SEQ 25], |
| GGGGCTGAGG ACCTGGTC | [SEQ 26] |
| ATACGGCCAG GCATTGAA | [SEQ 27], |
| CACTTGTGCC CTGACTTT | [SEQ 28], |
| CCTGGGGACC CTGGGCAA | [SEQ 29], |
| TGGTTGCCCA GGGTCCCC | [SEQ 30], |
| CCACTGACAA CCACCC | [SEQ 31], |
| CTCCCCTGCT TGCCACA | [SEQ 32], |
| TCAGCGGCAA GCAGAGG | [SEQ 33], |
| ATGGGACAGG TAGGACC | [SEQ 34], |
| CATAACTGCA CCCTTGG | [SEQ 35], |
| GGAGGAGACC AAGGGTGC | [SEQ 36], |
| GGAAACTTTC CACTTGA | [SEQ 37], |
| CCATCTTTTA ACTCAGGT | [SEQ 38], |
| CATGAAGGCA GGATGAG | [SEQ 39], |
| AGACCCTCTC ACTCATG | [SEQ 40], and |
| CAAGCAAGGG TTCAAAG | [SEQ 41]; | producing sequencing fragments by extension of the sequencing primer; and evaluating the length of the sequencing fragments to determine the sequence.

* * * * *